United States Patent
Weber

(10) Patent No.: US 8,058,593 B2
(45) Date of Patent: Nov. 15, 2011

(54) RESONATOR FOR MEDICAL DEVICE

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 291 days.

(21) Appl. No.: 12/551,153

(22) Filed: Aug. 31, 2009

(65) Prior Publication Data

US 2009/0319025 A1 Dec. 24, 2009

Related U.S. Application Data

(63) Continuation of application No. 11/136,259, filed on May 24, 2005, now Pat. No. 7,595,469.

(51) Int. Cl.
*H05B 6/10* (2006.01)
*A61F 2/06* (2006.01)
(52) U.S. Cl. ........................ 219/635; 623/1.1
(58) Field of Classification Search .......... 219/635, 219/636, 637, 638, 639, 640, 641, 642, 643, 219/644, 645; 623/1.1, 1.11, 1.15, 1.27, 623/1.3, 1.32, 1.44
See application file for complete search history.

(56) References Cited

U.S. PATENT DOCUMENTS

| | | |
|---|---|---|
| 5,409,460 A | 4/1995 | Krumme |
| 5,824,045 A | 10/1998 | Alt |
| 5,843,117 A | 12/1998 | Alt et al. |
| 5,855,600 A | 1/1999 | Alt |
| 5,871,437 A | 2/1999 | Alt |
| 6,027,510 A | 2/2000 | Alt |
| 6,053,873 A | 4/2000 | Govari et al. |
| 6,099,561 A | 8/2000 | Alt |
| 6,106,473 A | 8/2000 | Violante et al. |
| 6,159,142 A | 12/2000 | Alt |
| 6,159,237 A | 12/2000 | Alt et al. |
| 6,231,516 B1 | 5/2001 | Keilman et al. |
| 6,245,104 B1 | 6/2001 | Alt |
| 6,251,134 B1 | 6/2001 | Alt et al. |
| 6,280,385 B1 | 8/2001 | Melzer et al. |
| 6,304,769 B1 | 10/2001 | Arenson et al. |
| 6,387,121 B1 | 5/2002 | Alt |
| 6,398,805 B1 | 6/2002 | Alt |
| 6,416,540 B1 | 7/2002 | Mathur |
| 6,463,317 B1 | 10/2002 | Kucharczyk et al. |
| 6,478,815 B1 | 11/2002 | Alt |
| 6,511,325 B1 | 1/2003 | Lalka et al. |
| 6,516,213 B1 | 2/2003 | Nevo |

(Continued)

FOREIGN PATENT DOCUMENTS

WO WO 02/30331 4/2002

(Continued)

OTHER PUBLICATIONS

Busch, M., et al. "A Physical Explanation of Active MRI Stents (aMRIs) and first . . . ", Proceedings, Intl. Soc. for Magnetic Resonance in Medicine, vol. 10, May 18, 2002, 1 pg.

(Continued)

*Primary Examiner* — Daniel L Robinson
(74) *Attorney, Agent, or Firm* — Brooks, Cameron & Huebsch, PLLC

(57) ABSTRACT

A device resonator for medical device is provided. The resonator device includes a helical structure and a capacitor structure. The resonator device can be used in conjunction with a medical device, including a stent.

20 Claims, 6 Drawing Sheets

U.S. PATENT DOCUMENTS

| | | | |
|---|---|---|---|
| 6,574,497 B1 | 6/2003 | Pacetti | |
| 6,585,755 B2 | 7/2003 | Jackson et al. | |
| 6,652,540 B1 | 11/2003 | Cole et al. | |
| 6,668,197 B1 | 12/2003 | Habib et al. | |
| 6,673,104 B2 | 1/2004 | Barry | |
| 6,676,694 B1 | 1/2004 | Weiss | |
| 6,702,847 B2 | 3/2004 | DiCarlo | |
| 6,711,429 B1 | 3/2004 | Gilboa et al. | |
| 6,712,844 B2 | 3/2004 | Pacetti | |
| 6,716,237 B1 | 4/2004 | Alt | |
| 6,765,144 B1 | 7/2004 | Wang et al. | |
| 6,767,360 B1 | 7/2004 | Alt et al. | |
| 6,782,284 B1 | 8/2004 | Subramanyan et al. | |
| 6,786,904 B2 | 9/2004 | Doscher et al. | |
| 6,802,811 B1 | 10/2004 | Slepian | |
| 6,802,857 B1 | 10/2004 | Walsh et al. | |
| 6,808,535 B1 | 10/2004 | Jordan | |
| 6,844,492 B1 | 1/2005 | Wang et al. | |
| 6,847,837 B1 | 1/2005 | Melzer et al. | |
| 6,850,804 B2 | 2/2005 | Eggers et al. | |
| 6,884,234 B2 | 4/2005 | Aita et al. | |
| 6,892,090 B2 | 5/2005 | Verard et al. | |
| 6,908,468 B2 | 6/2005 | Daum | |
| 7,279,664 B2 * | 10/2007 | Weber | 219/635 |
| 7,595,469 B2 * | 9/2009 | Weber | 219/635 |
| 2001/0031919 A1 | 10/2001 | Strommer et al. | |
| 2001/0031920 A1 | 10/2001 | Kaufman et al. | |
| 2002/0019660 A1 | 2/2002 | Gianotti et al. | |
| 2002/0026230 A1 | 2/2002 | Moll et al. | |
| 2002/0049375 A1 | 4/2002 | Strommer et al. | |
| 2002/0082679 A1 | 6/2002 | Sirhan et al. | |
| 2002/0082685 A1 | 6/2002 | Sirhan et al. | |
| 2002/0137014 A1 | 9/2002 | Anderson et al. | |
| 2002/0188345 A1 | 12/2002 | Pacetti | |
| 2003/0004562 A1 | 1/2003 | DiCarlo | |
| 2003/0004563 A1 | 1/2003 | Jackson et al. | |
| 2003/0074049 A1 | 4/2003 | Hoganson et al. | |
| 2003/0083579 A1 | 5/2003 | Aita et al. | |
| 2003/0087244 A1 | 5/2003 | McCarthy | |
| 2003/0088178 A1 | 5/2003 | Owens et al. | |
| 2003/0088308 A1 | 5/2003 | Scheuermann et al. | |
| 2003/0092013 A1 | 5/2003 | McCarthy et al. | |
| 2003/0096248 A1 | 5/2003 | McCarthy et al. | |
| 2003/0099957 A1 | 5/2003 | McCarthy | |
| 2003/0100830 A1 | 5/2003 | Zhong et al. | |
| 2003/0105069 A1 | 6/2003 | Robinson et al. | |
| 2003/0139739 A1 | 7/2003 | Doscher et al. | |
| 2003/0143544 A1 | 7/2003 | McCarthy | |
| 2003/0144728 A1 | 7/2003 | Scheuermann et al. | |
| 2003/0187335 A1 | 10/2003 | McCarthy | |
| 2003/0199747 A1 | 10/2003 | Michlitsch et al. | |
| 2003/0212448 A1 | 11/2003 | Smith | |
| 2004/0010304 A1 | 1/2004 | Weber et al. | |
| 2004/0019376 A1 | 1/2004 | Alt | |
| 2004/0030379 A1 | 2/2004 | Hamm et al. | |
| 2004/0034300 A1 | 2/2004 | Verard et al. | |
| 2004/0038406 A1 | 2/2004 | Unger et al. | |
| 2004/0039438 A1 | 2/2004 | Alt | |
| 2004/0044397 A1 | 3/2004 | Stinson | |
| 2004/0059280 A1 | 3/2004 | Makower et al. | |
| 2004/0091603 A1 | 5/2004 | Priewe | |
| 2004/0093075 A1 | 5/2004 | Kuehne | |
| 2004/0097804 A1 | 5/2004 | Sobe | |
| 2004/0097805 A1 | 5/2004 | Verard et al. | |
| 2004/0098093 A1 | 5/2004 | DiCarlo | |
| 2004/0111016 A1 | 6/2004 | Casscells, III et al. | |
| 2004/0116997 A1 | 6/2004 | Taylor et al. | |
| 2004/0117007 A1 | 6/2004 | Whitbourne et al. | |
| 2004/0122494 A1 | 6/2004 | Eggers et al. | |
| 2004/0143180 A1 | 7/2004 | Zhong et al. | |
| 2004/0158310 A1 | 8/2004 | Weber et al. | |
| 2004/0186377 A1 | 9/2004 | Zhong et al. | |
| 2004/0243220 A1 | 12/2004 | Gianotti et al. | |
| 2004/0254632 A1 | 12/2004 | Alt et al. | |
| 2005/0004653 A1 | 1/2005 | Gerberding et al. | |
| 2005/0033407 A1 | 2/2005 | Weber et al. | |
| 2005/0065430 A1 | 3/2005 | Wiethoff et al. | |
| 2005/0065437 A1 | 3/2005 | Weber et al. | |
| 2005/0085895 A1 | 4/2005 | Brown et al. | |
| 2005/0131522 A1 | 6/2005 | Stinson et al. | |
| 2005/0143651 A1 | 6/2005 | Verard et al. | |
| 2005/0155779 A1 | 7/2005 | Wang et al. | |
| 2005/0165470 A1 | 7/2005 | Weber | |
| 2005/0178584 A1 | 8/2005 | Wang et al. | |

FOREIGN PATENT DOCUMENTS

| | | |
|---|---|---|
| WO | WO 2005/037143 | 4/2005 |

OTHER PUBLICATIONS

Melzer, A., et al. "Signal Enhancement of Stents in Magnetic Resonance Imaging". Proceedings of the Intl. Soc. for Magnetic Resonance in Medicine, Apr. 1, 2000, p. 1317.

Quick, H. H., et al. "Inductively coupled stent antennas in MRI". Magnetic Resonance in Medicine, vol. 48 No. 5, Nov. 2002 pp. 781-790.

Rainer, W., et al. "A new stent concept enables non-invasive MRI diagnostic . . .". Proceedings of the Intl. Soc. for Magnetic Rseonance in Medicine, May 18, 2002, 1 pg.

Truong, T., et al. "Susceptibility and shielding effects of metallic stents in CEMRA". Proceedings of the Intl. Soc. for Magnetic Resonance in Medicine, May 18, 2002, 1 pg.

International Search Report. Oct. 24, 2006, 5 pgs.

* cited by examiner

RESONATOR FOR MEDICAL DEVICE

PRIORITY INFORMATION

This application is a continuation of U.S. application Ser. No. 11/136,259, filed May 24, 2005, the specification of which is incorporated herein by reference.

FIELD OF THE INVENTION

The present invention relates generally to medical device apparatus, systems, and methods; and more particularly to medical device apparatus, systems, and methods for use during magnetic resonance imaging.

BACKGROUND

Stents and other metallic implants can cause a partial shielding of a radio frequency (RF) field by the Faraday Effect. In essences, the stent acts like a "Faraday Cage" that prevents the RF field from penetrating to the interior of the stent. Because stents are not ideal but only partial Faraday cages, a small percentage of the RF field still is able to penetrate to the interior, however not enough to cause enough spins to flip over and give a reasonable visibility.

One approach to achieving the reasonable visibility would be to raise the energy of the RF field (the flip-angle that stands for the duration of the RF-pulse) to such high levels that enough energy remains after passing through the partial stent shield for visualization. Unfortunately, taking this approach will cause the tissue of the body to be heated to unacceptable levels.

BRIEF DESCRIPTION OF THE DRAWINGS

The illustrations provided in the Figures are not to scale.

DETAILED DESCRIPTION

Figure 1:
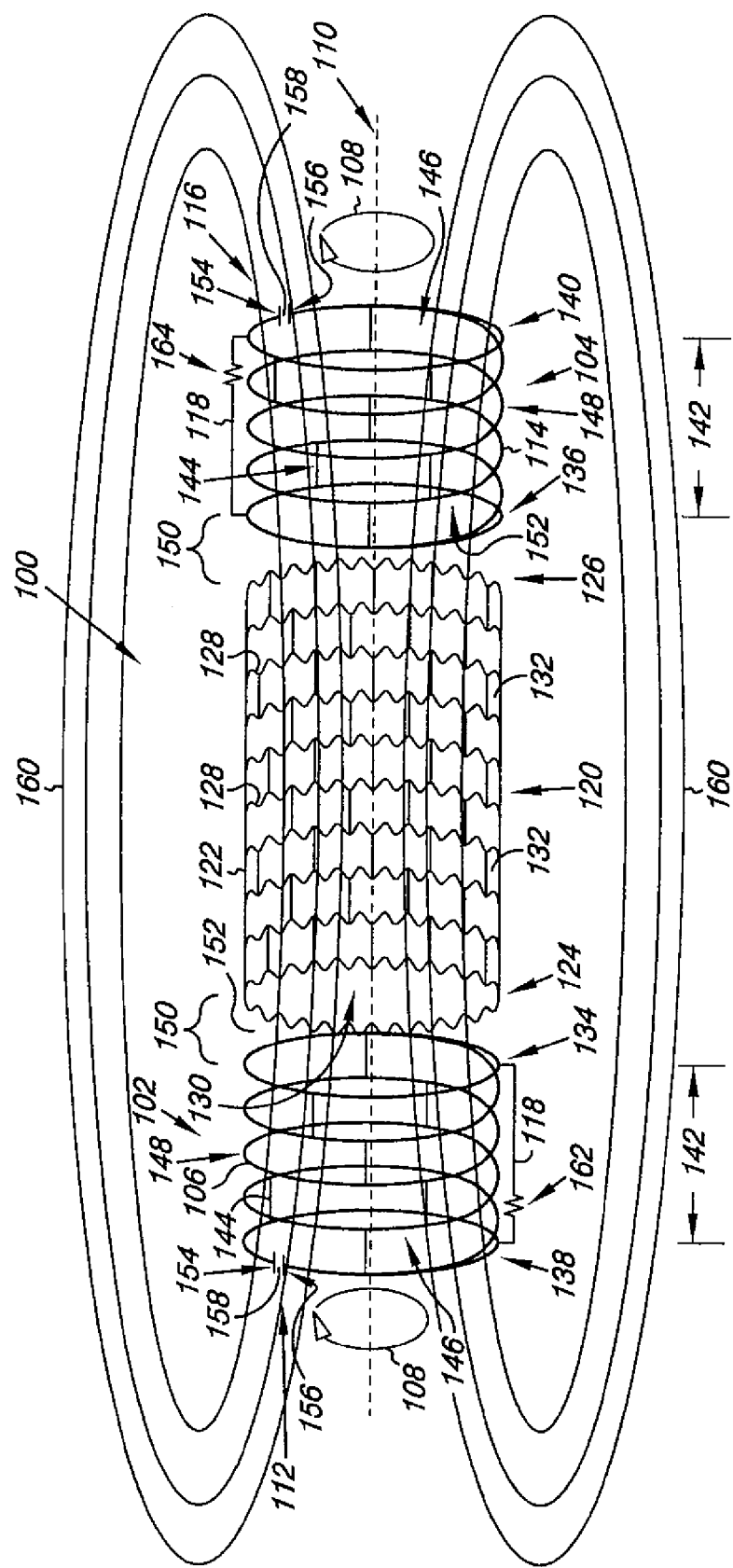
FIG. 1 illustrates an embodiment of a system including resonator devices according to the present invention.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments. In addition, discussion of features and/or attributes for an element with respect to one figure can also apply to the element shown in one or more additional figures.

Embodiments of the present invention are directed to medical device apparatus, systems, and methods of using the medical device. Generally, the medical device includes a resonator to be used in conjunction with an additional implantable medical device. These implantable medical devices include devices that traditionally have produced artifacts (signal loss) in images obtained by magnetic resonance imaging (MRI) systems. Embodiments of the present invention address the problem of artifacts (signal loss) produced in magnetic resonance (MR) images in addition to allowing for more complete MR images to be obtained from implantable medical devices.

Examples of such implantable medical devices include, but are not limited to, stents and/or shunts as are used in dialysis, artificial veins, arteries and grafts, esophageal stenosis, esophageal cancer, esophageal varacies, lung bronchi for cancer treatment, urethra, hydrocephalus shunt tubes, trachea, middle ear tubes, lymphatic ducts and grafts, gastrointestinal stenosis and inflammatory diseases (e.g. Crohn's disease), pyloric stenosis, implantable sensing devices, intravascular blood pressure devices, and biliary atresia. Examples of other types of implantable medical devices are also possible.

Typically, artifacts in MR images are due in large part to distortions in the magnetic field caused by the implanted medical device. For example, metallic stents can cause susceptibility and radiofrequency artifacts in MR images that do not allow for complete visualization of the stent lumen by magnetic resonance angiography (MRA). This is due to susceptibility artifacts and radiofrequency shielding of the metallic stents. Embodiments of the present invention can provide the potential for reduced artifacts during MR imaging with different MRA techniques through the use of a resonator device in conjunction with the second medical device (e.g., metallic vascular stent).

An additional issue is placement and effect of an implanted medical device in relation to biological structures surrounding the implanted medical device. For example, it would typically be desirable to minimize the effect of a vascular stent that traversed a bifurcation in the vasculature. Ideally it would be best not to further obstruct the side branch of the bifurcation with an additional structure that passes through or around the vascular stent. So, embodiments of the present invention provide for an induction coil to be positioned approximately adjacent each end of the vascular stent, where each induction coil is either part of a separate resonance circuit or combined in a single resonance circuit.

FIG. 1 illustrates one embodiment of a system 100 of the present invention. The system 100 includes a first resonator device 102 and a second resonator device 104. In one embodiment the first resonator device 102 includes a first induction coil 106 having at least one of a turn 108 of the electrically conductive coil 106. As used herein, a turn includes a complete revolution (i.e., at least 360 degrees) of the induction coil around a center axis 110. The first resonator device 102 further includes a first capacitor 112 coupled in series with the first induction coil 106. The second resonator device 104 of system 100 also includes at least one turn 108 of a second induction coil 114. The second resonator device 104 further includes a second capacitor 116 coupled in series with the second induction coil 114. Each of the first and second resonator devices 102, 104 further include a return conductor 118 to connect the ends of the induction coil and complete each of the respective resonator circuits.

The embodiment of system 100 further includes a stent 120. The stent 120 includes a tubular shaped body 122 having first and second ends 124 and 126 with elongate members 128 disposed between the first and second end 124 and 126. The tubular shaped body 122 of the stent 120 includes a surface defining a lumen 130 having a first diameter, d, that permits intraluminal delivery of the tubular shaped body 122 into a body passageway, e.g., a lumen of the vasculature. The tubular shaped body 122 can be expanded to a second diameter, d', from force applied to the tubular shaped body 122, where the second diameter d' can be variable in size depending upon the amount of force applied to the tubular shaped body 122. In one embodiment, the stent 120 can either be a balloon expandable stent or a self-expanding stent.

The elongate member 128 can be formed of a material which has the requisite strength and elasticity characteristics to permit the tubular shaped body 122 to be expanded from the first diameter, d, to the second diameter d'. The material also allows the tubular shaped body 122 to retain its expanded configuration with the second diameter, d'. Examples of such materials include, but are not limited to, metals and metal alloys including tantalum, stainless steel, titanium, a memory metal alloy (such as Nitinol), or any suitable plastic material having the requisite characteristics described herein.

The elongate member 128 can have a cylindrical cross-section, but as will be appreciated the elongate member 128 could have other cross-sectional configurations, such as triangular, square, rectangular, and/or hexagonal, among others. As illustrated, the elongate member 128 can be configured as a continuous helix of connected spirals or loops having a sinuous or zig-zag configuration. The elongate member 128 can also be fixedly secured to one another at predetermined intersection points and connectors 132 so as to help resist radial collapse of the stent 120 and to help maintain its enlarged second diameter, d'.

As illustrated, the stent 120 can be positioned adjacent the first resonator device 102 and the second resonator device 104. For example, at least one turn 108 of the first induction coil 106 extends beyond the first end 124 away from the second end 126 of the stent 120. Similarly, at least one turn 108 of the second induction coil 114 extends from the second end 126 away from the first end 124 of the stent 120.

As discussed herein, the first and second induction coils 106, 114 and the first and second capacitors 112, 116 of the first and second resonator devices 102, 104 can interact with a radio frequency field of a magnetic resonance imaging (MRI) system to reduce signal loss in MR images. So, for example, the first and second resonator devices 102, 104 can be used in combination with, for example, the stent 120 (e.g., a metallic vascular stent) that if used alone would produce an artifact (signal loss) in MR images obtained by the MRI system.

As illustrated, the first and second induction coils 106, 114 include an elongate configuration that extends circumferentially from a first end 134, 136 to a second end 138, 140 of the respective first and second resonator devices 102, 104. For example, each of the first and second induction coils 106, 114 can have a helical structure as illustrated in FIG. 1 that extends from the first end 134, 136 to the second end 138, 140 of the first and second resonator devices 102, 104. In one embodiment, coils of the helical structure can be equally spaced from each other. In an alternative embodiment, coils of the helical structure can have a predetermined non-consistent spacing relative to each other along the helical structure.

In one embodiment, the first and second induction coils 106, 114 can extend continuously down a length 142 of the first and second resonator devices 102, 104 (i.e., the induction coils 106, 114 do not deviate along the length 142 of the first and second resonator devices 102, 104). Alternatively, the first and second induction coils 106, 114 can include a "zig-zag" configuration as the first and second induction coils 106, 114 extends down the length 142 of the first and/or second resonator device 102, 104. As will be appreciated, other shapes and configurations that can act as an induction coil, besides helical coils, are also possible.

The first and second induction coils 106, 114 can be formed of one or more conductive members (e.g., two or more members in parallel). In addition, different cross-sectional geometries can be used for the first and second induction coils 106, 114. For example, the cross-sectional geometries can include circular rectangular, oval and/or polygonal, among others. Other shapes are also possible.

The conductive members of the first and second induction coils 106, 114 can also have a number of different sizes and structural configurations. For example, the conductive members can have a size and a shape sufficient to maintain a predetermined shape of the first and second induction coils 106, 114 in its deployed state. Alternatively, the size and the shape of each of the first and second induction coils 106, 114 and a structural support, as will be discussed herein, are configured to maintain the predetermined shape of the first and second induction coils 106, 114 in its deployed state.

In one embodiment, the conductive members of the first and second induction coils 106, 114 can be a metal or metal alloy. Examples of such metals and metal alloys include, but are not limited to, platinum, titanium, stainless steel (e.g., 316L stainless steel), and memory metals alloys such as Nitinol, titanium-palladuim-nickel, nickel-titanium-copper, gold-cadmium, iron-zinc-copper-aluminum, titanium-niobium-aluminum, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible.

In addition, one or more of the components of the first and/or second resonator devices 102, 104 can be made radioopaque. For example, one or more portions of the first and second induction coils 106, 114 could be clad with a radioopaque material to make the first and/or second resonator devices 102, 104 radioopaque. Alternatively, one or more discrete radioopaque markers having a predetermined shape can be added to predetermined portions of the first and/or second resonator devices 102, 104. Examples of suitable materials for the radioopaque markers include, but are not limited to, copper, tungsten, gold, silver, platinum and alloys thereof. Other materials are also possible.

The first and second induction coils 106, 114 can further include spacers 144 positioned between the turns 108 of the first and second induction coils 106, 114. In one embodiment, the spacers 144 provide for electrical insulation, structural support, and structural spacing for adjacent turns 108 of the coils 106, 114. Examples of suitable materials for the spacers 144 include, but are not limited to non-biodegradable and/or biodegradable materials.

Examples of non-biodegradable materials include, but are not limited to, polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersons (BAYHDROL); squalene emulsions; and mixtures and copolymers of any of the foregoing.

Examples of biodegradable materials include, but are not limited to, polycarboxylic acid, polyanhydrides including maleic anhydride polymers; polyorthoesters; poly-amino acids; polyethylene oxide; polyphosphazenes; polyactic acid, polyglycolic acid and copolymers and copolymers and mixtures thereof such as poly(L-lactic acid) (PLLA), poly (D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and poly-dimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The spacers 144 can further include one or more therapeutic agents. In one embodiment, the one or more therapeutic agents can be integrated into the material matrix of and/or coated on the surface of the spacers 144. The one or more therapeutic agents can then leach and/or be released from the spacers 144 once implanted.

Examples of therapeutic agents include, but are not limited to, pharmaceutically acceptable agents such as non-genetic therapeutic agents, a biomolecule, a small molecule, or cells. Exemplary non-genetic therapeutic agents include anti-thrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin−) cells including Lin-CD34−, Lin-CD34+, Lin-cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

The elongate configuration of the first and second induction coils 106, 114 also define a coil lumen 146 and a peripheral surface 148 opposite the lumen 146. The induction coil 102, the capacitor 104 and the structural support 106 are configured to allow the lumen 146 to expand from a first cross-sectional size in an un-deployed state to a second cross-sectional size in a deployed state. This allows the first and second resonator devices 102, 104 to be introduced into a body with the first cross-sectional size and then be expanded to the second cross-sectional size at the predetermined location within the body. For example, one or both of the first and second resonator devices 102, 104 can be positioned over a balloon of a balloon catheter in its first cross-sectional size (e.g., its un-deployed configuration).

The balloon can then be inflated to expand the first and second resonator devices 102, 104 to its second cross-sectional size (e.g., its deployed configuration). Alternatively, when the induction coils 106, 114 is formed of a memory metal alloy (such as Nitinol), the first and second resonator devices 102, 104 can be introduced into the body in its first cross-sectional size (e.g., its un-deployed configuration) and then released to expand the first and second resonator devices 102, 104 to its second cross-sectional size (e.g., its deployed configuration).

In one embodiment, the first and second resonator devices 102, 104 are electrically isolated from the stent 120. For example, the first end 134 of the first resonator device 102 can be adjacent the first end 124 of the stent 120, where a predetermined gap 150 exists between the ends 124 and 134. Similarly, the first end 136 of the second resonator device 104 can be adjacent the second end 126 of the stent 120, where the predetermined gap 150 exists between the ends 126 and 136. In one embodiment, the predetermined gap 150 is sufficiently large to allow the first and second resonator devices 102, 104 to be physically and electrically isolated (i.e., separated) from the stent 120.

As will be appreciated, the present embodiment allows the first and second resonator devices 102, 104 to be used in conjunction with the stent 120 that may or may not already be implanted into the body. For example, the first and second resonator devices 102, 104 could be implanted adjacent the stent 120 that is already in position within a patient. Alternatively, the first and second resonator devices 102, 104 could be positioned relative the stent 120 prior to their implantation. The devices could then be implanted together, although not necessarily at the exact same time. Examples of such configurations are discussed herein.

As will be appreciated, each of the first and second induction coils 106, 114 includes loops 152 of electrically conductive material that in conjunction with the respective first and second capacitor 112, 116 can be used to tune the respective resonator device 102, 104 to a predetermined radio frequency (RF). Examples of parameters used in tuning the resonator devices 102, 104 include, but are not limited to, the number of turns 108, and the cross sectional area of each induction coil 106, 114 of the respective resonator device 102, 104. In one embodiment, the number of turns 108 of the first and/or second induction coil 106, 114 can be modified based on a configuration of each induction coil 106, 114.

The configuration of the first and/or second capacitor 112, 116 for the respective resonator device 102, 104 can also be modified in tuning the resonator device 102, 104. For example, each of the capacitors 112, 116 can include at least a first capacitor plate 154, a second capacitor plate 156 and a dielectric material 158 disposed between the first and second capacitor plates 154 and 156. Predetermined modifications to the size, shape, distance between the capacitor plates and dielectric material configuration, for example, can allow for adjustments to be made in the tuning of each resonator device 102, 104.

As will be appreciated, a plate structure need not be used for the first and second capacitor plate 154 and 156, as other shapes for the capacitor plates are possible. For example, helical coils of conductive material separated by the dielectric can be used in forming the capacitor plates. Alternatively, fractal capacitor structures could be used in providing the first and/or second capacitor 112, 116. In addition, each of the resonator devices 102, 104 can further include an auto-tuning circuit so as to provide additional tuning of the capacitor and/or the resonator device 102, 104 due to, for example, changes in the diameter of the induction coil.

As illustrated, the system 100 includes two separate resonator devices 102, 104. As will be appreciated, as there are two separate resonator devices, the resonance frequencies of each device needs to be matched to the Larmor frequency of the MRI system (e.g., 64 Mz at 1.5 T). However, given the situation where one of the induction coils 106, 114 will most likely be smaller in diameter than the other induction coil, there will be a difference in the induction value (L) and consequently in the capacitance value (C). The resonance frequency (F) is given by the inverse square root of the product LC $$F = 1/(2 \cdot (\pi) \cdot (L \cdot C)^{0.5})$$

The magnetic field B 160 on the axis 110 of a coil 106, 114 falls with distance x from the coil 106, 114 according to the relationship:

$$B = \mu_0 \cdot N \cdot I \cdot r^2 / (2(r^2 + x^2) \cdot 1.5 \text{ Tesla}$$

Where N is the number of turns 108, I is the current in the coil, and r is the coil radius.

In the case of two different coils 106, 114 located a distance from each other but aligned along the same axis 110, so called Helmholtz coils, the magnetic field 160 can be extended homogeneously in between the two coils 106, 114. If the second coil 114 is placed at a distance r from the first coil 106, a near uniform field 160 can be produced in the central region between the coils 106, 114. As will be appreciated, this Helmholtz construction can be used as well for non-bifurcated vessels in which a stent is positioned in between two coils distally and proximally of the stent. This might aid in reducing the thickness of the implant at the site of the stent.

As illustrated, each of the resonator devices 102, 104 also includes the return conductor 118 that couples each respective capacitor 112, 116 positioned near the second end 138, 140 in series to the induction coil 106, 114 that extends between the first and second ends. In one embodiment, the return conductor 118 can be positioned adjacent the peripheral surface 148 of the induction coil 106, 114. In an alternative embodiment, the return conductor 118 can be positioned within the lumen 146 of the induction coil 106, 114.

In an additional embodiment, one or both of the resonator devices 102, 104 can also include a resistor coupled in series with the induction coil and capacitor. In one embodiment, the use of a resistor in the resonator circuit allows for an inductive response across a wider spectrum of RF energies. For example, the first resonator device 102 can include a first resistor 162 in series with the first capacitor 112 and first induction coil 106, and the second resonator device 104 can include a second resistor 164 in series with the second capacitor 116 and second induction coil 114. Other configurations are also possible.

As illustrated in FIG. 1, the first resonator device 102, the second resonator device 104 and the stent 120 while being in a general proximity to each other are physically and electrically separate from each other. Additional embodiments of the present invention include configurations in which the first and second resonator devices 102, 104 and the stent 120 are physically and/or electrically coupled to each other.

Figure 2:
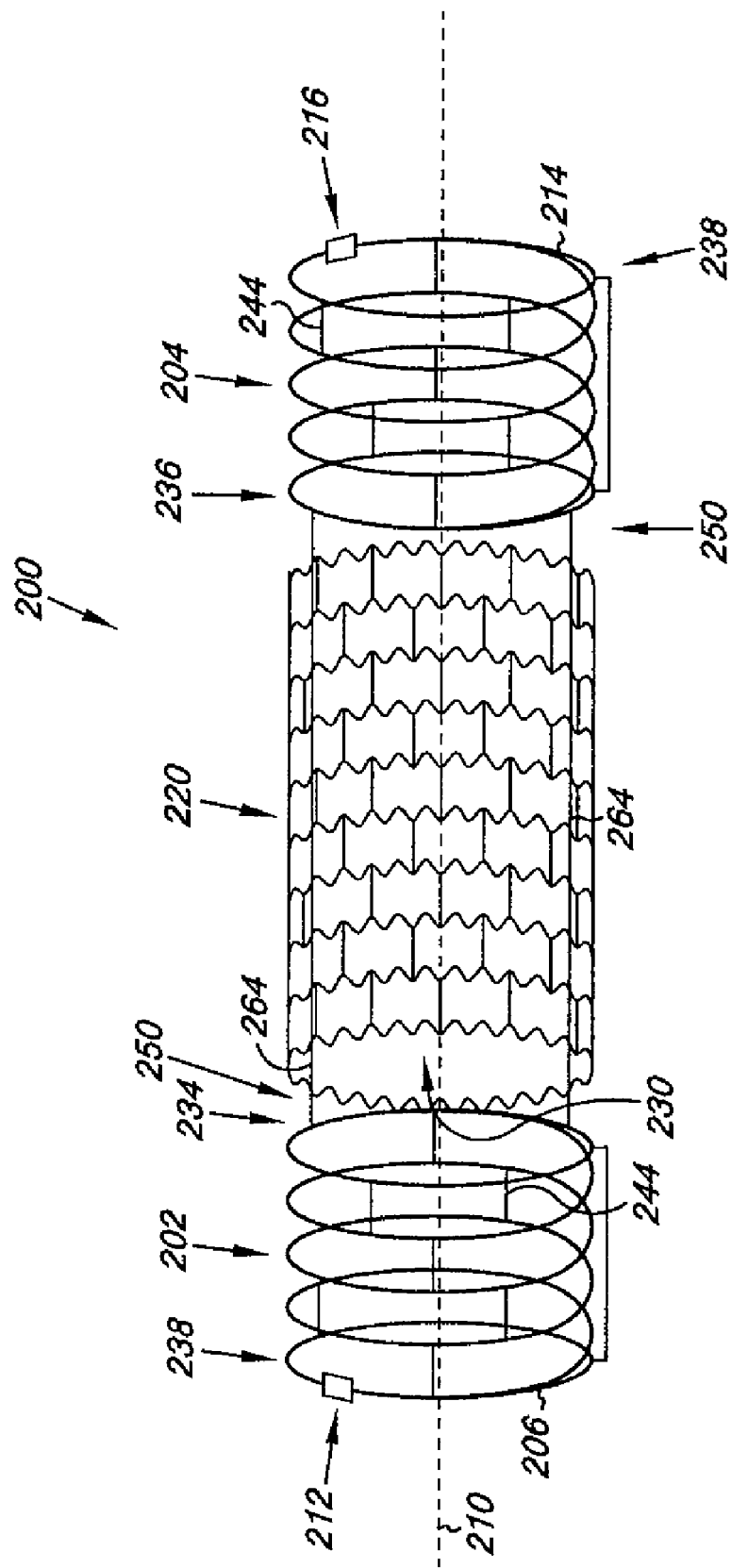
FIG. 2 illustrates an embodiment of a system including resonator devices according to the present invention.

FIG. 2 provides an additional illustration of the system 200 of the present invention. The system 200 includes the first resonator device 202 and the second resonator device 204, as discussed here. In addition, the system 200 includes a connection member 264 that separates and couples the first resonator device 202 and the second resonator device 204. As illustrated, the system 200 includes two of the connection member 264 that couple the first and second resonator devices 202, 204 through the stent 220. As will be appreciated, a single connection member 264 could also be used to couple the resonator devices 202, 204. In one embodiment, use of a single connection member 264 can allow the resonator devices 202, 204 to be positioned relative the stent 202, as discussed herein, along a center axis 210 that may not be linear (i.e., that includes at least one curve).

In one embodiment, the connection member 264 can be constructed of the same material as the first and second induction coils 206, 214. Alternatively, the connection member 264 can be constructed of a material that is different (e.g., different conductivity, flexibility, malleability, stiffness) than the material used for the first and second induction coils 206, 214. In addition, the connection member 264 can have a number of different cross-sectional profiles, including but not limited to, circular, oval, triangular, and polygonal. The cross-sectional area of the connection member 264 can also be greater than or equal to that of the first and second induction coils 206, 214. For example, the connection member 264 could have a diameter that is greater than or equal to the diameter of the first and second induction coils 206, 214. In an alternative embodiment, the cross-sectional area of the connection member 264 can be less than or equal to that of the first and second induction coils 206, 214.

As illustrated, the connection member 264 can be an elongate member that passes through the lumen 230 of the stent 220. In an alternative embodiment, the connection member 264 can be in the form of a helix that extends between the first and second resonator devices 202, 204. The connection member 264 can also be sheathed with an electrical insulator (e.g., e-PTFE or pyrolene) to electrically insulate the first and second resonator devices 202, 204 from the stent 220. In one embodiment, the electrical insulator can also serve to electrically insulate the connection member 264 from the first and second resonator devices 202, 204. In addition, one or more portions of the connection member 264 could be made radioopaque, as discussed herein.

In one embodiment, the connection member 264 has a length that is sufficient to position the first and second resonator devices 202, 204 relative the stent 220, as discussed herein. For example, the length and configuration of the elongate body for the connection member 264 as sufficient to ensure the predetermined gap 250 is created.

The connection member 264 can also be coupled to the resonator devices 202, 204 in a number of ways. For example, a chemical adhesive and/or a mechanical fastener could be used to couple the connection member 264 to the resonator devices 202, 204. Examples of mechanical fasteners include, but are not limited to compressive sleeves, welding, and/or physical integration (e.g., twisting or braiding together). In an alternative embodiment, In an alternative embodiment, the connection member 264 and one or more of the resonator devices 202, 204 can be formed from a single piece of material. For example, the connection member 264 and one of the first or second induction coil 206, 214 could be cut (laser or water cut) from a single tube of material. Alternatively, the connection member 264 and one of the first or second induction coil 206, 214 could be formed from a single length of material. Connection members 264 could be equally space around the first or second induction coil 206, 214. Alternatively, two or more connection members 264 could be unequally spaced around the first or second induction coil 206, 214.

Figure 3:
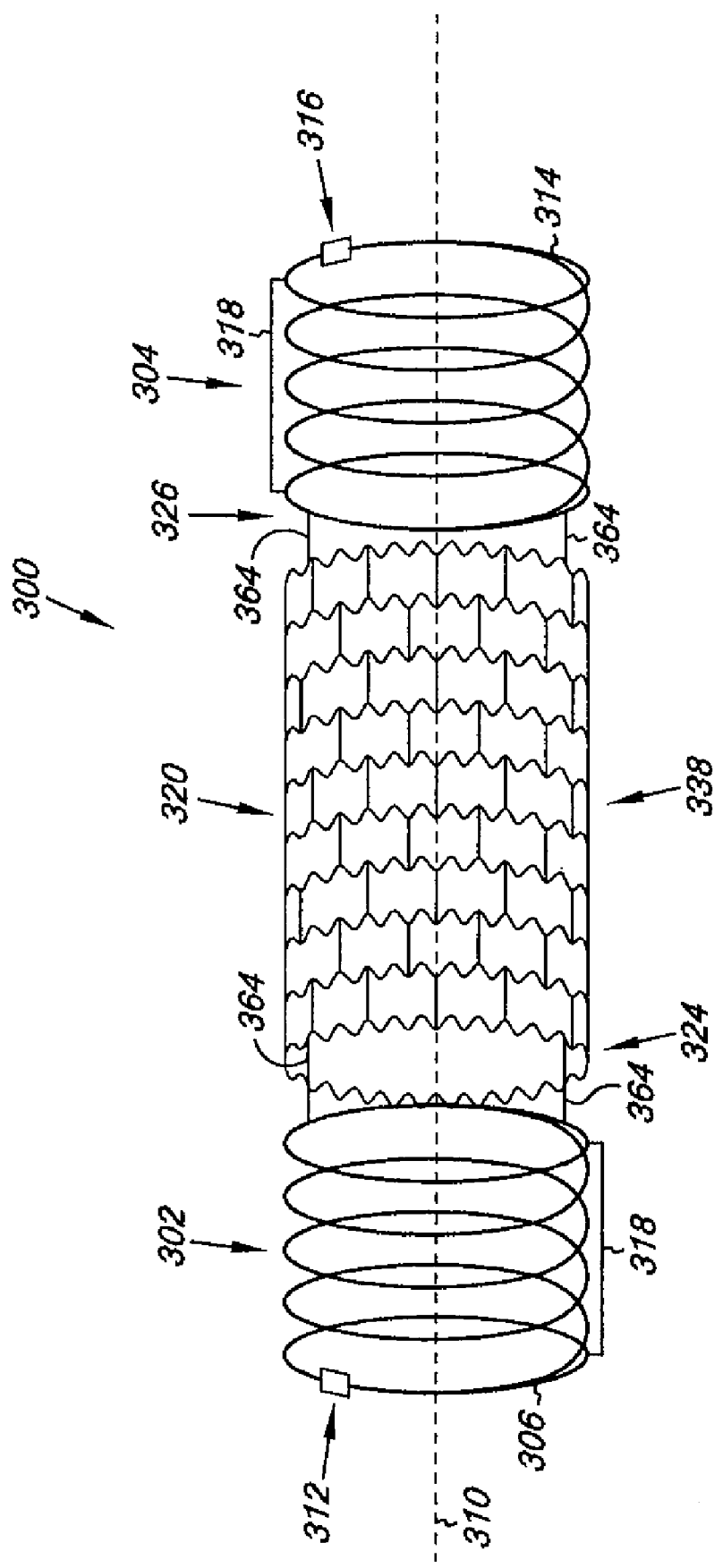
FIG. 3 illustrates an embodiment of a system including resonator devices according to the present invention.

FIG. 3 provides an additional embodiment of the system 300 according to the present invention. The system 300 includes the first and second resonator device 302, 304, as discussed here. In addition, the system 300 includes the connection member 364 that separates and couples the first and second resonator device 302, 304 through the stent 320. As illustrated, the connection member 364 couples the first resonator device 302 to the first end 324 of the stent 320 and the second resonator device 304 to the second end 326 of the stent 320. The system 300 also includes a configuration in which two or more of the connection member 364 are used to couple the resonator devices 302, 304 to the stent 320. In an alternative embodiment, one connection member 364 could be used to couple each of the resonator devices 302, 304 to the stent 320.

FIG. 3 also illustrates an additional embodiment of the circuit configuration of the system 300. For example, the first induction coil 306 and the second induction coil 314 can be coupled in series through the connection member 364 and the first capacitor 312. In this configuration, the system 300 includes the first and second induction coil 306, 314, the connection member 364 and the first capacitor 312 coupled in series to complete the induction circuit. In an additional embodiment, the system 300 can further include a resistor in series with the first and second induction coil 306, 314, the connection member 364 and the first capacitor 312. FIG. 3 also provides an embodiment in which the first and second induction coil 306, 314 are coupled in series through the connection member 364, the first capacitor 312, and the stent 320. In other words, the stent 320 is used as a conductor for completing the induction circuit. As will be appreciated, a predetermined portion of the stent 320 can be configured as the portion of the stent 320 that completes the circuit.

Figure 4:
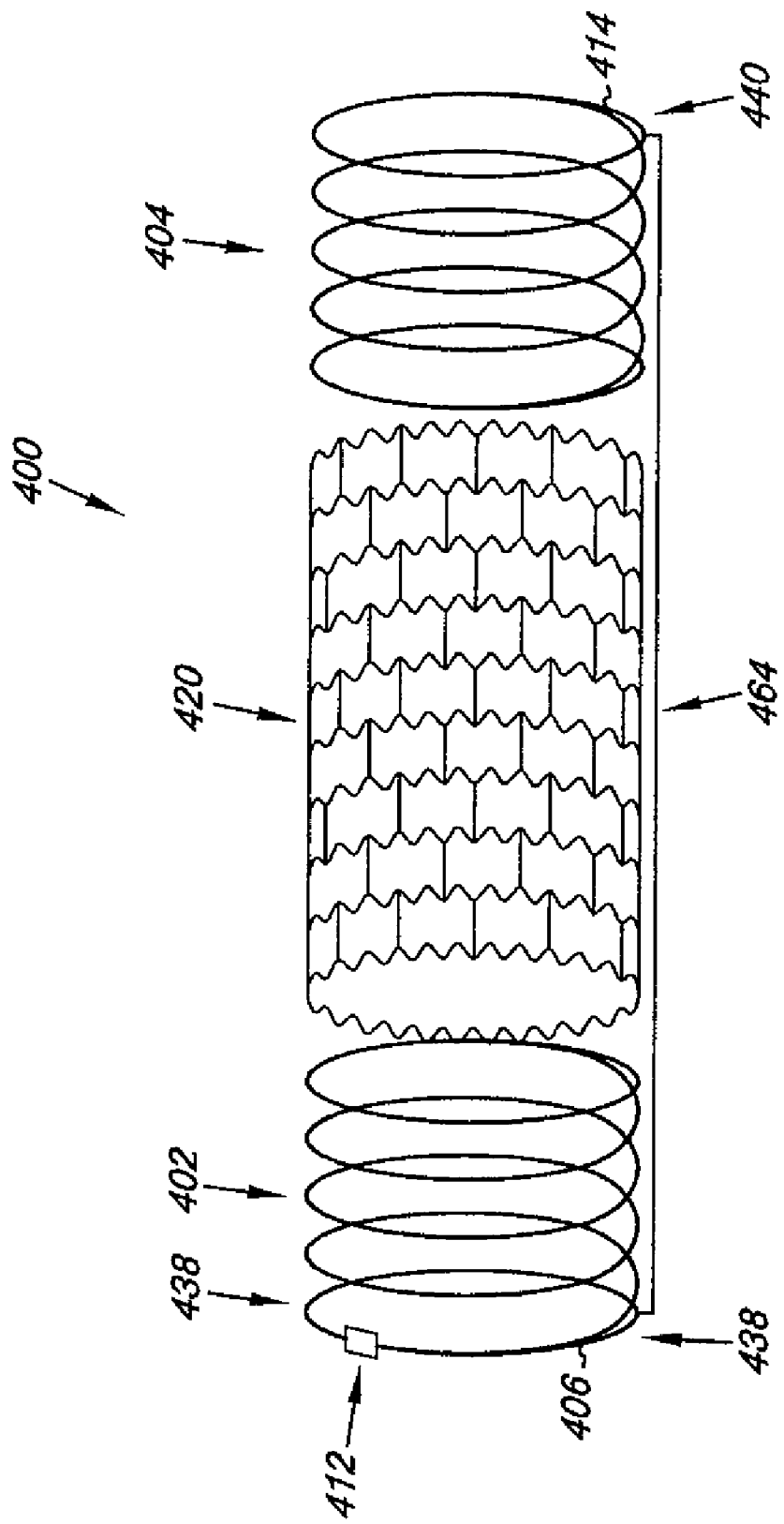
FIG. 4 illustrates an embodiment of a system including resonator devices according to the present invention.

FIG. 4 provides an additional embodiment of the system 400 according to the present invention. The system 400 includes the first and second resonator device 402, 404, as discussed here. In addition, the system 400 includes the connection member 464 that separates and couples the first and second resonator device 402, 404. As illustrated, the connection member 464 extends past an exterior surface of the stent 420.

The connection member 464 can be an elongate member that passes over the exterior surface of the stent 420. In an alternative embodiment, the connection member 464 can be in the form of a helix that extends between the first and second resonator devices 402, 404. The connection member 464 can also be sheathed with an electrical insulator (e.g., e-PTFE or pyrolene) to electrically insulate the first and second resonator devices 402, 404 from the stent 420. In one embodiment, the electrical insulator can also serve to electrically insulate the connection member 464 from the first and second resonator devices 402, 404. In addition, one or more portions of the connection member 464 could be made radioopaque, as discussed herein.

In the present embodiment, the connection member 464 also severs to electrically couple the first and second induction coils 406, 414 (turning in the same direction) and the first capacitor 412 in series. As illustrated, the connection member 464 can, for example, extend from the second end 438 of the first coil 406 to the second end 440 of the second coil 414. For example, the connection member 464 and the first coil 406 could be formed from a single tube of material (e.g., laser or water cut), where the connection member 464 would then be bent back over the first coil 406 to extend and be attached to the second coil 414 so as to complete the circuit.

Figure 5:
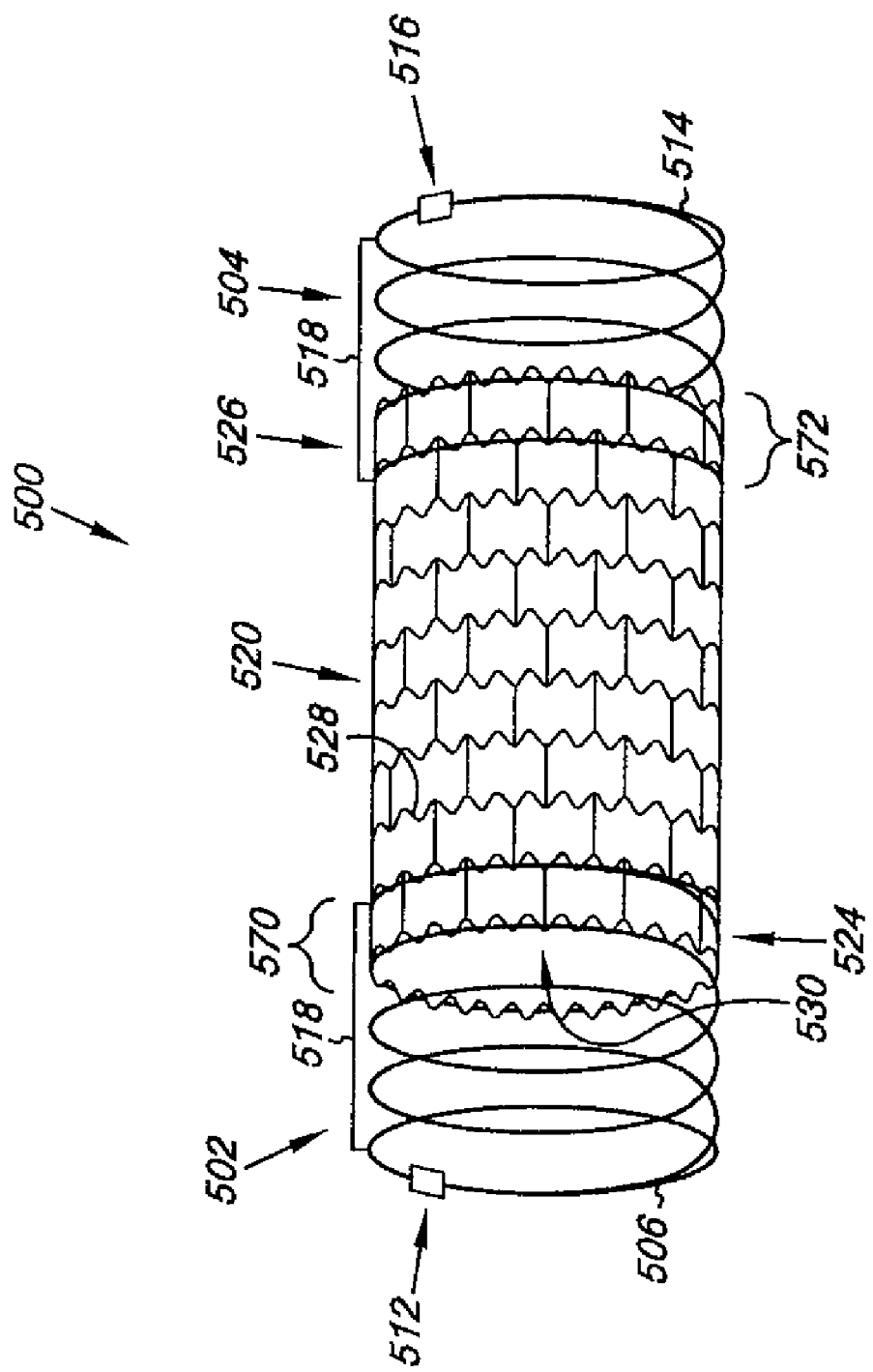
FIG. 5 illustrates an embodiment of a system including resonator devices according to the present invention.

FIG. 5 provides an additional embodiment of the system 500 according to the present invention. The system 500 includes the first and second resonator device 502, 504 and the stent 520, as discussed here. As illustrated, at least a predetermined portion of each of the induction coils 506, 514 are positioned over the stent 520. For example, at least a portion of the first induction coil 506 can be positioned over a first portion 570 of the stent 520 and at least a portion of the second induction coil 514 can be positioned over a second portion 572 of the stent 520. As illustrated, the first and second portions of the stent 570, 572 can include portions of the stent 520 that are adjacent the first end 524 and the second end 526 of the stent 520.

In one embodiment, the induction coils 506, 514 interact with the stent 520 through a mechanical interaction (e.g., a compressive friction fit). Alternatively, the induction coils 506, 514 could be woven through openings defined by the elongate members 528 of the stent 520. In addition, the induction coils 506, 514 can also be sheathed with an electrical insulator (e.g., e-PTFE or pyrolene) to electrically isolate the first and second resonator devices 502, 504 from the stent 520. When electrically isolated from the stent 520, each of the first and second resonator devices 502, 504 includes the first capacitor 512 and the second capacitor 516, respectively, coupled in series with their respective induction coil 506, 514.

In an alternative embodiment, the second induction coil 514 can be coupled in series with the first induction coil 506 and the first capacitor 512 of the first resonator device 502. In one embodiment, coupling the second induction coil 514 in series with the first resonator device 502 can be accomplished by using the stent 520 as a conductor, as described herein, or through the use of a connection member, as discussed herein.

As will be appreciated, the induction coils 506, 514 could also be partially positioned within the lumen 530 of the stent 520, where at least a portion of the induction coils 506, 514 extend from the end 524, 526 of the stent 520. In addition, it is possible that one of the induction coils 506, 514 for the first and second resonator device 502, 504 can be positioned on the peripheral surface of the stent 520 and the other in the lumen 530 of the stent 520, as discussed herein. In addition, one or more portions of the resonator devices 502, 504 and/or the stent 520 could be made radioopaque, as discussed herein.

Figure 6:
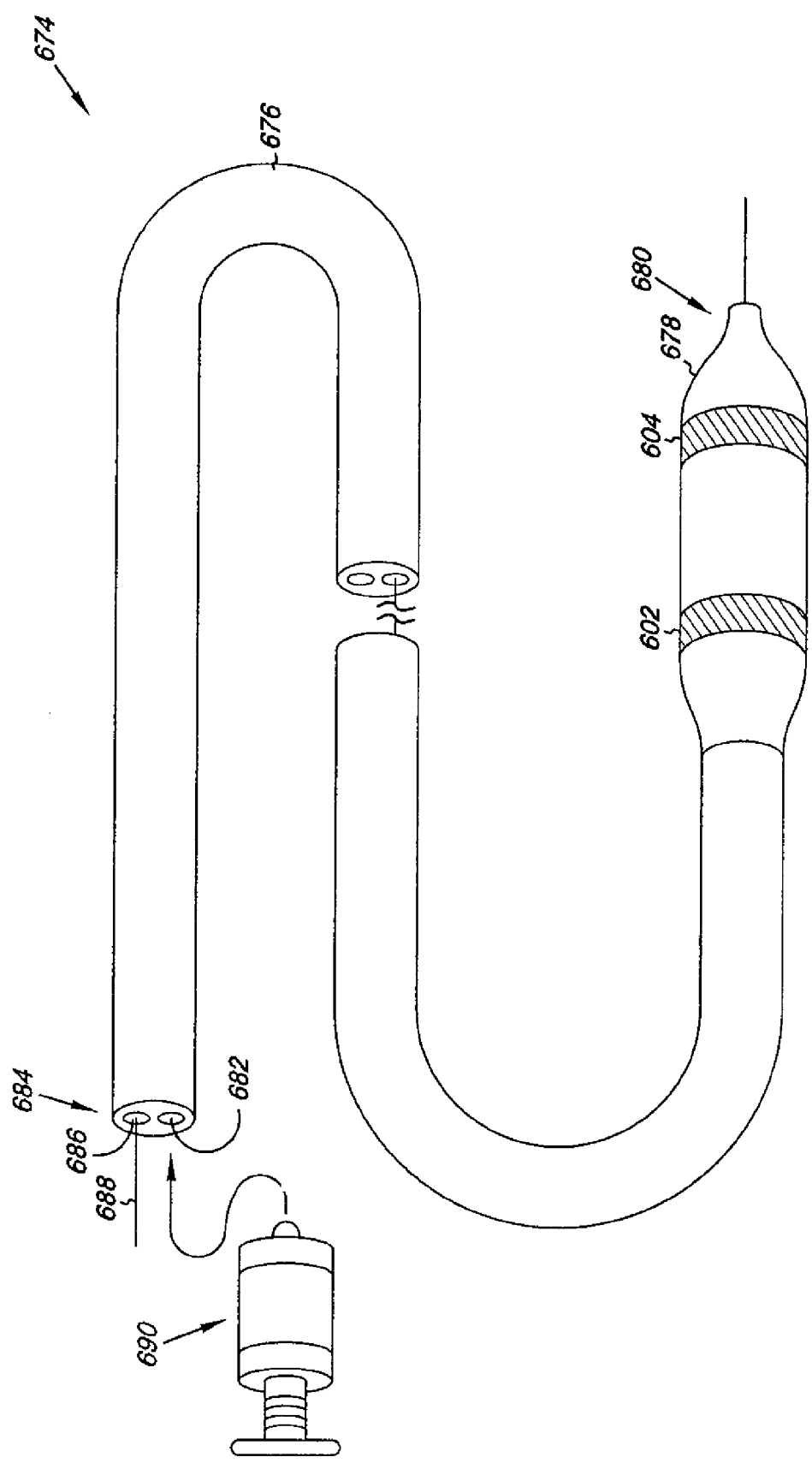
FIG. 6 illustrates an embodiment of a balloon catheter and a system including resonator devices according to the present invention.

FIG. 6 illustrates a system having a catheter 674 with an elongate body 676, an inflatable balloon 678 positioned adjacent a distal end 680, and a lumen 682 longitudinally extending in the elongate body 676 of the catheter 674 from the inflatable balloon 678 to a proximal end 684. In the present example, the inflatable balloon 678 can be at least partially positioned within the lumen 646 of the first and/or second resonator device 602, 604.

The catheter 674 can further include a guidewire lumen 686 to receive a guidewire 688. Guidewire 688 and guidewire lumen 686 assist in positioning the resonator devices 602, 604, as discussed herein, at a predetermined location within the body. Once in position, the inflatable balloon 678 can be inflated through the use of an inflation pump 690 that can releasably couple to the lumen 682. As the inflatable balloon 678 inflates, the resonator devices 602, 604 expand to the second diameter, as discussed herein, so as to position the resonator devices 602, 604 in the patient.

As discussed herein, embodiments of the resonator device and the stent can be implanted into a body. As will be appreciated, a variety of procedures can be used to implant an embodiment of the resonator device in association with the stent. For example, certain embodiments of the resonator device can be implanted adjacent a stent that has already been implanted in a body. Alternatively, both the stent and certain embodiments of the resonator device can be implanted simultaneously. For example, both the stent and the resonator device could be loaded onto an implant catheter (e.g., a balloon catheter) for implanting in the body.

Embodiments of the present invention further include methods for tuning of the implanted resonator devices discussed herein. For example, in embodiments in which the resonator devices are electrically isolated from each other across the stent, the two independent resonator devices may resonate at two separate frequencies or frequency ranges. As will be appreciated, it is advantageous to have both resonator devices tuned to resonate at the same frequencies or frequency ranges.

In one embodiment, tuning the resonator devices to resonate at the same frequencies or frequency ranges includes implanting a first resonator device and a stent into a body lumen. As discussed herein, the first of a resonator device as discussed herein and the stent can be implanted through the use of a balloon catheter. The frequency response of the implanted first resonator device and stent can then be measured. Based on the measured frequency response, the second resonator device can be modified.

In one embodiment, modifying the frequency response of the second resonator device can include changing or modifying one or more physical parameters of the second resonator device. For example, the frequency response of the second resonator device can be modified by changing a capacitance value of the second resonator device, as discussed herein. In addition, the frequency response of the second resonator device can be modified by modifying an induction coil of the second resonator device. For example, the number, diameter and/or density of loops for the induction coil could be modified to tune the second resonator device. In addition, the size of a resistor used in series with the second resonator device could also be modified in tuning the second resonator device.

The second resonator device can then be implanted in proximity to the first resonator device and the stent. In their implanted position, the first resonator device and the second resonator device can produce a resonant radio frequency field that is focused through the lumen of the stent. This then allows for images from within the lumen of the stent to be derived based on the resonant radio frequency field focused through the lumen of the stent.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the resonator device can be coated with a non-thrombogenic biocompatible material, as are known or will be known, one or more pharmaceuticals and/or biological compounds or molecules. Embodiments and illustrations described herein can further be modified and/or added to according to copending U.S. patent application Ser. No. 09/779,204, entitled "Vascular Stent with Composite Structure for Magnetic Reasonance Imaging Capabilities" [sic], and U.S. patent application Ser. No. 11/207,304, entitled "Resonator for Medical Device" (e.g., the structural support structure described therein), which are both incorporated herein by reference in its entirety.

What is claimed is:

1. A method, comprising:
   implanting a first resonator device and a stent;
   measuring the frequency response of the first resonator device and the stent;
   modifying a second resonator device based on the measured frequency response of the first resonator device and the stent; and
   implanting the second resonator device in proximity to the first resonator device and the stent.

2. The method of claim 1, where modifying the second resonator device includes changing a capacitance value of the second resonator device.

3. The method of claim 1, where modifying the second resonator device includes modifying an induction coil of the second resonator device.

4. The method of claim 1, where modifying the second resonator device includes modifying a resistor in the second resonator device.

5. The method of claim 1, including producing a resonant radio frequency field with the first resonator device and the second resonator device.

6. The method of claim 5, including focusing the resonant radio frequency field through a lumen of the stent.

7. The method of claim 6, including deriving images from within the lumen of the stent based on the resonant radio frequency field focused through the lumen of the stent.

8. The method of claim 1, including positioning at least a portion of the first induction coil over a first portion of the stent.

9. The method of claim 1, where the first resonator device includes a first induction coil and a second induction coil coupled in series, and where the second induction coil extends beyond a first end away from a second end of the stent.

10. A method, comprising:
    implanting a first resonator device and a stent, where the first resonator device includes a first induction coil with at least one turn and the stent includes a first end and a second end, and where at least one turn of the first induction coil extends beyond the first end away from the second end of the stent;
    measuring the frequency response of the first resonator device and the stent;
    modifying a second resonator device based on the measured frequency response of the first resonator device and the stent, where the second resonator device includes a second induction coil with at least one turn; and
    implanting the second resonator device in proximity to the first resonator device and the stent.

11. The method of claim 10, including coupling the first induction coil and the second induction coil in series through a connection member and a first capacitor.

12. The method of claim 11, including coupling the first induction coil and the second induction coil in series through the connection member, the first capacitor, and a resistor.

13. The method of claim 11, including coupling the first induction coil and the second induction coil in series through the connection member, the first capacitor, and the stent.

14. The method of claim 11, including coupling the first induction coil and the second induction coil in series through the connection member, the first capacitor, the stent, and a resistor.

15. The method of claim 10, where at least one turn of the second induction coil extends from the second end away from the first end of the stent.

16. A method, comprising:
    implanting a first resonator device and a stent, where the first resonator device is adjacent a first end of the stent;
    measuring the frequency response of the first resonator device and the stent;
    modifying a second resonator device based on the measured frequency response of the first resonator device and the stent; and
    implanting the second resonator device in proximity to the first resonator device and the stent, where the second resonator device is adjacent a second end of the stent.

17. The method of claim 16, where the first resonator device and the second resonator device are physically and electrically isolated from the stent.

18. The method of claim 16, where a connection member separates and couples the first resonator device and the second resonator device through the stent.

19. The method of claim 18, where the connection member extends through a lumen of the stent.

20. The method of claim 18, where the connection member extends past an exterior surface of the stent.

* * * * *